US012383687B2

(12) United States Patent
Veliss et al.

(10) Patent No.: US 12,383,687 B2
(45) Date of Patent: Aug. 12, 2025

(54) INTERFACE INCLUDING A FOAM CUSHIONING ELEMENT

(71) Applicant: ResMed Pty Ltd, Bella Vista (AU)

(72) Inventors: Lee James Veliss, Rotterdam (NL); Renee Frances Doherty, Eastwood (AU); Scott Alexander Howard, Sydney (AU); Alicia Kristianne Wells, Sydney (AU); Fiona Catherine Carroll, Hawkesbury (AU); David Mark Gilliver, Black Rock (AU); Brett Thomas Lindsay, Melbourne (AU)

(73) Assignee: ResMed Pty Ltd, Bella Vista (AU)

( * ) Notice: Subject to any disclaimer, the term of this patent is extended or adjusted under 35 U.S.C. 154(b) by 1062 days.

(21) Appl. No.: 17/377,558

(22) Filed: Jul. 16, 2021

(65) Prior Publication Data
US 2021/0338957 A1    Nov. 4, 2021

Related U.S. Application Data

(63) Continuation of application No. 15/987,734, filed on May 23, 2018, now Pat. No. 11,077,277, which is a (Continued)

(30) Foreign Application Priority Data
Mar. 4, 2008 (AU) .............................. 2008901056

(51) Int. Cl.
A61M 16/06 (2006.01)
A61M 16/10 (2006.01)
A62B 18/08 (2006.01)

(52) U.S. Cl.
CPC ........ A61M 16/06 (2013.01); A61M 16/0622 (2014.02); A61M 16/0633 (2014.02); A61M 16/106 (2014.02); A62B 18/084 (2013.01)

(58) Field of Classification Search
CPC .. A41D 13/1176; A61F 11/08; A61L 2430/14; A61L 27/18; A61M 16/06;
(Continued)

(56) References Cited

U.S. PATENT DOCUMENTS 2,931,356 A    4/1960   Schwarz
3,787,895 A    1/1974   Belvedere
(Continued)

FOREIGN PATENT DOCUMENTS

AU    199651130    10/1996
AU    2005100738   11/2005
(Continued)

OTHER PUBLICATIONS

NZ First Examination Report mailed Dec. 24, 2020 in related NZ application 770159 (3 pages).
(Continued)

Primary Examiner — Annette Dixon
(74) Attorney, Agent, or Firm — Nixon & Vanderhye P.C.

(57) ABSTRACT

A respiratory mask assembly includes a frame having a channel and a cushioning element including a clip portion adapted for interference seal and retention in the channel. The cushioning element includes an interfacing portion constructed from foam and having a wider width than the clip portion.

19 Claims, 9 Drawing Sheets

Related U.S. Application Data continuation of application No. 12/736,030, filed as application No. PCT/AU2009/000262 on Mar. 4, 2009, now Pat. No. 9,987,450.

(58) Field of Classification Search
CPC .......... A61M 16/0605; A61M 16/0616; A61M 16/0622; A61M 16/0633; A61M 16/0638; A61M 16/0644; A61M 16/065; A61M 16/0666; A61M 16/0672; A61M 16/0683; A61M 16/0688; A61M 16/08; A61M 16/0816; A61M 2205/02; A61M 2205/0216; A61M 2205/0266; A61M 2210/0618; A62B 18/025; A62B 18/08; A62B 18/084; C08L 75/04; Y10S 24/48; Y10T 24/45529

See application file for complete search history.

(56) References Cited

U.S. PATENT DOCUMENTS

| | | |
|---|---|---|
| 3,815,596 A | 6/1974 | Keener et al. |
| 3,974,829 A | 8/1976 | Tate |
| 4,405,212 A | 9/1983 | Cooper |
| 4,653,124 A | 3/1987 | McNeal |
| D293,613 S | 1/1988 | Wingler |
| 4,755,040 A | 7/1988 | Haslbeck |
| 4,782,832 A | 11/1988 | Trimble |
| 4,960,121 A * | 10/1990 | Nelson ................. A62B 18/025 D24/110.4 |
| D333,015 S | 2/1993 | Farmer et al. |
| 5,188,123 A * | 2/1993 | Gardner, Jr. ............ A61F 11/08 128/864 |
| 5,375,593 A | 12/1994 | Press |
| 5,385,141 A | 1/1995 | Granatiero |
| 5,394,568 A | 3/1995 | Brostrom et al. |
| 5,396,885 A | 3/1995 | Nelson |
| 5,398,676 A | 3/1995 | Press et al. |
| 5,400,776 A | 3/1995 | Bartholomew |
| 5,419,318 A | 5/1995 | Tayebi |
| 5,425,359 A | 6/1995 | Liou |
| 5,429,683 A | 7/1995 | Le Mitouard |
| 5,437,267 A | 8/1995 | Weinstein et al. |
| 5,441,046 A | 8/1995 | Starr et al. |
| 5,462,528 A | 10/1995 | Roewer |
| 5,477,852 A | 12/1995 | Landis et al. |
| 5,488,948 A | 2/1996 | Dubruille et al. |
| 5,509,409 A | 4/1996 | Weatherholt |
| 5,513,634 A | 5/1996 | Jackson |
| 5,513,635 A | 5/1996 | Bedi |
| 5,526,806 A | 6/1996 | Sansoni |
| 5,533,506 A | 7/1996 | Wood |
| 5,538,000 A | 7/1996 | Rudolph |
| 5,538,001 A | 7/1996 | Bridges |
| 5,540,223 A | 7/1996 | Starr et al. |
| 5,560,354 A | 10/1996 | Berthon-Jones et al. |
| 5,570,684 A | 11/1996 | Behr |
| 5,592,938 A | 1/1997 | Scarberry et al. |
| 5,623,923 A | 4/1997 | Bertheau et al. |
| 5,647,357 A | 7/1997 | Barnett et al. |
| 5,653,228 A | 8/1997 | Byrd |
| 5,655,527 A | 8/1997 | Scarberry et al. |
| 5,660,174 A * | 8/1997 | Jacobelli ........... A61M 16/0616 128/206.24 |
| 5,662,101 A | 9/1997 | Ogden et al. |
| 5,682,881 A | 11/1997 | Winthrop et al. |
| 5,704,345 A | 1/1998 | Berthon-Jones et al. |
| 5,707,342 A | 1/1998 | Tanaka |
| 5,724,965 A | 3/1998 | Handke et al. |
| 5,735,272 A | 4/1998 | Dillon et al. |
| 5,740,799 A | 4/1998 | Nielson |
| 5,752,511 A | 5/1998 | Simmons et al. |
| 5,794,619 A | 8/1998 | Edeiman et al. |
| 5,807,341 A | 9/1998 | Heim |
| 5,842,469 A | 12/1998 | Rapp et al. |
| 5,906,203 A | 5/1999 | Klockseth et al. |
| 5,918,598 A | 7/1999 | Belfer et al. |
| 5,921,239 A | 7/1999 | McCall et al. |
| 5,954,049 A | 9/1999 | Foley et al. |
| 5,975,079 A | 11/1999 | Hellings et al. |
| 6,019,101 A | 2/2000 | Cotner et al. |
| 6,026,811 A | 2/2000 | Settle |
| 6,044,844 A | 4/2000 | Kwok et al. |
| 6,082,360 A | 7/2000 | Rudolph et al. |
| 6,086,118 A | 7/2000 | McNaughton et al. |
| 6,095,996 A | 8/2000 | Steer et al. |
| 6,098,205 A | 8/2000 | Schwartz et al. |
| 6,109,263 A | 8/2000 | Feuchtgruber |
| 6,112,746 A | 9/2000 | Kwok et al. |
| 6,119,693 A | 9/2000 | Kwok et al. |
| 6,119,694 A | 9/2000 | Correa et al. |
| 6,123,071 A | 9/2000 | Berthon-Jones et al. |
| 6,123,082 A | 9/2000 | Berthon-Jones |
| 6,139,787 A | 10/2000 | Harrison |
| 6,152,137 A | 11/2000 | Schwartz et al. |
| 6,193,914 B1 | 2/2001 | Harrison |
| 6,196,223 B1 | 3/2001 | Belfer et al. |
| 6,211,263 B1 | 4/2001 | Cinelli et al. |
| 6,231,548 B1 | 5/2001 | Bassett |
| 6,241,930 B1 | 6/2001 | Harrison |
| 6,258,066 B1 | 7/2001 | Urich |
| 6,295,366 B1 | 9/2001 | Haller et al. |
| 6,328,038 B1 | 12/2001 | Kessler et al. |
| 6,341,606 B1 | 1/2002 | Bordewick et al. |
| 6,347,631 B1 | 2/2002 | Hansen et al. |
| 6,357,441 B1 | 3/2002 | Kwok et al. |
| 6,358,279 B1 | 3/2002 | Tahi et al. |
| 6,374,826 B1 | 4/2002 | Gunaratnam et al. |
| 6,397,847 B1 | 6/2002 | Scarberry |
| 6,412,487 B1 * | 7/2002 | Gunaratnam ...... A61M 16/0638 128/205.25 |
| 6,412,488 B1 | 7/2002 | Barnett et al. |
| 6,412,593 B1 | 7/2002 | Jones |
| 6,419,660 B1 | 7/2002 | Russo |
| 6,422,238 B1 | 7/2002 | Lithgow |
| 6,423,036 B1 | 7/2002 | Van Huizen |
| 6,431,172 B1 | 8/2002 | Bordewick |
| 6,434,796 B1 | 8/2002 | Speirs |
| 6,439,234 B1 | 8/2002 | Curti et al. |
| 6,448,303 B1 | 9/2002 | Paul |
| 6,467,482 B1 | 10/2002 | Boussignac |
| 6,467,483 B1 | 10/2002 | Kopacko et al. |
| 6,470,887 B1 | 10/2002 | Martinez |
| 6,478,026 B1 | 11/2002 | Wood |
| 6,482,178 B1 | 11/2002 | Andrews et al. |
| 6,491,034 B1 | 12/2002 | Gunaratnam et al. |
| 6,513,526 B2 | 2/2003 | Kwok et al. |
| 6,530,373 B1 | 3/2003 | Patron et al. |
| 6,532,961 B1 | 3/2003 | Kwok et al. |
| 6,536,435 B1 | 3/2003 | Fecteau et al. |
| 6,561,188 B1 | 5/2003 | Ellis |
| 6,561,190 B1 | 5/2003 | Kwok et al. |
| 6,561,192 B2 | 5/2003 | Palmer |
| 6,561,193 B1 | 5/2003 | Noble |
| 6,571,798 B1 | 6/2003 | Thornton |
| 6,579,267 B2 | 6/2003 | Lynch et al. |
| 6,581,601 B2 | 6/2003 | Ziaee |
| 6,581,602 B2 | 6/2003 | Kwok et al. |
| 6,584,975 B1 | 7/2003 | Taylor |
| 6,595,214 B1 | 7/2003 | Hecker et al. |
| 6,595,215 B2 | 7/2003 | Wood |
| 6,607,516 B2 | 8/2003 | Cinelli et al. |
| 6,615,832 B1 * | 9/2003 | Chen ..................... A62B 18/08 128/206.28 |
| 6,627,289 B1 | 9/2003 | Dilnik et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,655,385 B1 | 12/2003 | Curti et al. |
| 6,663,600 B2 | 12/2003 | Bierman et al. |
| 6,669,712 B1 | 12/2003 | Cardoso |
| D485,905 S | 1/2004 | Moore et al. |

(56) References Cited

U.S. PATENT DOCUMENTS

| | | |
|---|---|---|
| 6,679,257 B1 | 1/2004 | Robertson et al. |
| 6,679,265 B2 | 1/2004 | Strickland et al. |
| 6,701,927 B2 | 3/2004 | Kwok et al. |
| 6,710,099 B2 | 3/2004 | Cinelli et al. |
| 6,766,800 B2 | 7/2004 | Chu et al. |
| 6,766,817 B2 | 7/2004 | da Silva |
| 6,776,162 B2 | 8/2004 | Wood |
| 6,776,163 B2 | 8/2004 | Dougill et al. |
| 6,789,543 B2 | 9/2004 | Cannon |
| 6,805,117 B1 | 10/2004 | Ho et al. |
| 6,807,967 B2 | 10/2004 | Wood |
| 6,817,362 B2 | 11/2004 | Gelinas et al. |
| 6,820,617 B2 | 11/2004 | Robertson et al. |
| 6,823,865 B2 | 11/2004 | Drew et al. |
| 6,823,869 B2 | 11/2004 | Raje et al. |
| 6,834,650 B1 | 12/2004 | Fini |
| 6,851,429 B2 * | 2/2005 | Bishop ............... A41D 13/1176 |
| | | 128/206.25 |
| 6,860,270 B2 | 3/2005 | Sniadach |
| 6,895,965 B2 | 5/2005 | Scarberry et al. |
| 6,907,882 B2 | 6/2005 | Ging et al. |
| 6,918,404 B2 | 7/2005 | Dias da Silva |
| 6,926,004 B2 | 8/2005 | Schumacher |
| 6,938,620 B2 | 9/2005 | Payne, Jr. |
| 6,968,844 B2 | 11/2005 | Liland |
| 6,972,003 B2 | 12/2005 | Bierman et al. |
| 6,986,352 B2 | 1/2006 | Frater et al. |
| 6,997,177 B2 | 2/2006 | Wood |
| 7,011,090 B2 | 3/2006 | Drew et al. |
| 7,018,362 B2 | 3/2006 | Bierman et al. |
| 7,021,311 B2 | 4/2006 | Gunaratnam et al. |
| 7,052,127 B2 | 5/2006 | Harrison |
| 7,066,586 B2 | 6/2006 | da Silva |
| 7,076,282 B2 | 7/2006 | Munro et al. |
| 7,080,645 B2 | 7/2006 | Genger et al. |
| 7,101,359 B2 | 9/2006 | Kline et al. |
| 7,107,989 B2 | 9/2006 | Frater et al. |
| 7,146,976 B2 | 12/2006 | McKown |
| 7,152,599 B2 | 12/2006 | Thomas |
| 7,152,601 B2 | 12/2006 | Barakat et al. |
| 7,191,781 B2 | 3/2007 | Wood |
| 7,207,328 B1 | 4/2007 | Altemus |
| 7,207,334 B2 | 4/2007 | Smart |
| 7,210,481 B1 | 5/2007 | Lovell et al. |
| 7,237,551 B2 | 7/2007 | Ho et al. |
| 7,243,723 B2 | 7/2007 | Surjaatmadja |
| D550,836 S | 9/2007 | Chandran et al. |
| D552,733 S | 10/2007 | Criscuolo et al. |
| 7,285,255 B2 | 10/2007 | Kadlec et al. |
| 7,287,528 B2 | 10/2007 | Ho |
| 7,302,950 B2 | 12/2007 | Berthon-Jones et al. |
| 7,318,437 B2 | 1/2008 | Gunaratnam et al. |
| 7,318,439 B2 | 1/2008 | Raje |
| 7,523,754 B2 | 4/2009 | Lithgow |
| 7,658,189 B2 | 2/2010 | Davidson |
| 8,146,595 B2 * | 4/2012 | Sherman ............ A61M 16/0683 |
| | | 24/DIG. 48 |
| 8,245,711 B2 | 8/2012 | Matula |
| 8,490,623 B2 | 7/2013 | Berthon-Jones et al. |
| 8,684,004 B2 | 4/2014 | Eifler |
| 8,701,667 B1 | 4/2014 | Ho et al. |
| 9,937,312 B2 | 4/2018 | Kwok |
| 9,987,450 B2 | 6/2018 | Veliss et al. |
| 10,265,489 B2 | 4/2019 | Wells |
| 2001/0020474 A1 | 9/2001 | Hecker et al. |
| 2002/0005198 A1 | 1/2002 | Kwok et al. |
| 2002/0029780 A1 | 3/2002 | Frater et al. |
| 2002/0046755 A1 | 4/2002 | DeVoss |
| 2002/0053347 A1 | 5/2002 | Ziaee |
| 2002/0066452 A1 | 6/2002 | Kessler et al. |
| 2002/0069872 A1 | 6/2002 | Gradon et al. |
| 2002/0096178 A1 | 7/2002 | Ziaee |
| 2002/0124849 A1 | 9/2002 | Billette De Villemeur |
| 2002/0143296 A1 | 10/2002 | Russo |
| 2002/0157673 A1 | 10/2002 | Kessler et al. |
| 2002/0174868 A1 | 11/2002 | Kwok et al. |
| 2002/0185134 A1 | 12/2002 | Bishop |
| 2003/0000526 A1 | 1/2003 | Goebel |
| 2003/0019495 A1 | 1/2003 | Palkon et al. |
| 2003/0019496 A1 | 1/2003 | Kopacko et al. |
| 2003/0034034 A1 * | 2/2003 | Kwok ............... A61M 16/0622 |
| | | 128/207.13 |
| 2003/0075180 A1 | 4/2003 | Raje et al. |
| 2003/0079749 A1 | 5/2003 | Strickland et al. |
| 2003/0089373 A1 | 5/2003 | Gradon |
| 2003/0111080 A1 | 6/2003 | Olsen et al. |
| 2003/0154980 A1 | 8/2003 | Berthon-Jones et al. |
| 2003/0168063 A1 * | 9/2003 | Gambone ......... A61M 16/0605 |
| | | 128/203.16 |
| 2003/0196656 A1 | 10/2003 | Moore et al. |
| 2003/0196658 A1 | 10/2003 | Ging et al. |
| 2004/0025882 A1 | 2/2004 | Madaus et al. |
| 2004/0025885 A1 | 2/2004 | Payne, Jr. |
| 2004/0045551 A1 | 3/2004 | Eaton et al. |
| 2004/0065328 A1 | 4/2004 | Amarasinghe et al. |
| 2004/0106891 A1 | 6/2004 | Langan et al. |
| 2004/0107968 A1 | 6/2004 | Griffiths |
| 2004/0111104 A1 | 6/2004 | Schein et al. |
| 2004/0112384 A1 | 6/2004 | Lithgow et al. |
| 2004/0118406 A1 | 6/2004 | Lithgow et al. |
| 2004/0127856 A1 | 7/2004 | Johnson |
| 2004/0133958 A1 | 7/2004 | Darnell et al. |
| 2004/0211428 A1 | 10/2004 | Jones |
| 2004/0226564 A1 | 11/2004 | Persson |
| 2004/0226566 A1 | 11/2004 | Gunaratnam et al. |
| 2005/0011523 A1 | 1/2005 | Aylsworth et al. |
| 2005/0028822 A1 | 2/2005 | Sleeper et al. |
| 2005/0033247 A1 | 2/2005 | Thompson |
| 2005/0039757 A1 | 2/2005 | Wood |
| 2005/0051171 A1 | 3/2005 | Booth |
| 2005/0051176 A1 | 3/2005 | Riggins |
| 2005/0056286 A1 | 3/2005 | Huddart et al. |
| 2005/0061326 A1 | 3/2005 | Payne, Jr. |
| 2005/0101933 A1 | 5/2005 | Marrs et al. |
| 2005/0121030 A1 | 6/2005 | Bateman |
| 2005/0150495 A1 | 7/2005 | Rittner et al. |
| 2005/0155604 A1 | 7/2005 | Ging et al. |
| 2005/0172969 A1 | 8/2005 | Ging et al. |
| 2005/0199239 A1 | 9/2005 | Lang et al. |
| 2005/0211252 A1 | 9/2005 | Lang et al. |
| 2005/0241644 A1 | 11/2005 | Gunaratnam et al. |
| 2005/0257792 A1 | 11/2005 | Wixey et al. |
| 2005/0284481 A1 | 12/2005 | Meyer |
| 2006/0042629 A1 | 3/2006 | Geist |
| 2006/0060200 A1 | 3/2006 | Ho et al. |
| 2006/0081250 A1 | 4/2006 | Bordewick et al. |
| 2006/0095008 A1 | 5/2006 | Lampropoulos et al. |
| 2006/0095009 A1 | 5/2006 | Lampropoulos et al. |
| 2006/0096598 A1 | 5/2006 | Ho et al. |
| 2006/0107960 A1 | 5/2006 | Smart |
| 2006/0118117 A1 | 6/2006 | Berthon-Jones |
| 2006/0124131 A1 | 6/2006 | Chandran et al. |
| 2006/0137690 A1 | 6/2006 | Gunaratnam et al. |
| 2006/0174887 A1 | 8/2006 | Chandran et al. |
| 2006/0207597 A1 | 9/2006 | Wright |
| 2006/0207599 A1 | 9/2006 | Busch et al. |
| 2006/0237017 A1 | 10/2006 | Davidson et al. |
| 2006/0237018 A1 | 10/2006 | McAuley et al. |
| 2006/0283461 A1 | 12/2006 | Lubke et al. |
| 2006/0289010 A1 | 12/2006 | Kwok et al. |
| 2007/0023044 A1 | 2/2007 | Kwok et al. |
| 2007/0044804 A1 | 3/2007 | Matula |
| 2007/0125387 A1 | 6/2007 | Zollinger et al. |
| 2007/0144525 A1 | 6/2007 | Davidson et al. |
| 2007/0186930 A1 | 8/2007 | Davidson et al. |
| 2007/0221227 A1 | 9/2007 | Ho |
| 2007/0272249 A1 | 11/2007 | Chandran et al. |
| 2007/0282272 A1 | 12/2007 | Bannon et al. |
| 2008/0004573 A1 | 1/2008 | Kaufmann et al. |
| 2008/0006277 A1 | 1/2008 | Worboys et al. |
| 2008/0047560 A1 | 2/2008 | Veliss et al. |
| 2008/0060649 A1 | 3/2008 | Veliss et al. |
| 2008/0065022 A1 | 3/2008 | Kyvik et al. |
| 2008/0110469 A1 | 5/2008 | Weinberg |

(56) References Cited

U.S. PATENT DOCUMENTS

| | | |
|---|---|---|
| 2008/0149104 A1 | 6/2008 | Eifler |
| 2008/0200880 A1 | 8/2008 | Kyvik et al. |
| 2008/0257354 A1 | 10/2008 | Davidson et al. |
| 2009/0014007 A1 | 1/2009 | Brambilla et al. |
| 2009/0044808 A1 | 2/2009 | Guney et al. |
| 2010/0000534 A1 | 1/2010 | Kooij et al. |
| 2010/0018534 A1 | 1/2010 | Veliss et al. |
| 2010/0326445 A1 | 12/2010 | Veliss et al. |
| 2018/0264217 A1 | 9/2018 | Veliss et al. |

FOREIGN PATENT DOCUMENTS

| | | |
|---|---|---|
| CN | 1628870 | 6/2005 |
| CN | 1681553 | 10/2005 |
| CN | 1784250 A | 6/2006 |
| CN | 1901962 | 1/2007 |
| CN | 101128233 A | 2/2008 |
| CN | 101155610 | 4/2008 |
| CN | 101155618 | 4/2008 |
| CN | 101389369 | 3/2009 |
| DE | 185017 | 5/1907 |
| DE | 30 11 900 | 10/1980 |
| DE | 146 688 | 2/1981 |
| DE | 37 19 009 | 12/1988 |
| DE | 39 27 038 | 2/1991 |
| DE | 297 23 101 | 7/1998 |
| DE | 197 03 526 | 8/1998 |
| DE | 199 44 242 | 3/2001 |
| DE | 10002571 | 7/2001 |
| DE | 102 13 905 | 10/2002 |
| DE | 10 2004 055 433 | 11/2004 |
| EP | 0 288 937 | 11/1988 |
| EP | 0 427 474 | 5/1991 |
| EP | 0 466 960 | 1/1992 |
| EP | 0 303 090 | 4/1992 |
| EP | 0 658 356 | 6/1995 |
| EP | 0 776 679 | 6/1997 |
| EP | 1 099 452 | 5/2001 |
| EP | 1 147 782 A2 | 10/2001 |
| EP | 1 258 266 | 11/2002 |
| EP | 1 481 702 | 12/2004 |
| EP | 1 982 740 A2 | 10/2008 |
| EP | 2 259 828 | 12/2010 |
| FR | 2 720 280 | 12/1995 |
| GB | 532214 | 1/1941 |
| GB | 2 176 404 | 12/1986 |
| GB | 2 368 533 | 5/2002 |
| GB | 2 385 533 | 8/2003 |
| JP | 2000-515784 | 11/2000 |
| JP | 2005-529687 | 10/2005 |
| JP | 2006-326129 | 12/2006 |
| NZ | 553756 | 6/2007 |
| WO | WO 1982/003548 | 10/1982 |
| WO | WO 1987/001950 | 4/1987 |
| WO | WO 1992/020392 | 11/1992 |
| WO | WO 1992/020395 | 11/1992 |
| WO | WO 1996/028207 | 9/1996 |
| WO | WO 1998/004310 | 2/1998 |
| WO | WO 1998/012965 | 4/1998 |
| WO | WO 1998/023305 | 6/1998 |
| WO | WO 1999/016327 | 4/1999 |
| WO | WO 1999/025410 | 5/1999 |
| WO | WO 1999/043375 | 9/1999 |
| WO | WO 1999/061088 | 12/1999 |
| WO | WO 2000/020072 | 4/2000 |
| WO | WO 2000/038772 | 7/2000 |
| WO | WO 2000/050121 | 8/2000 |
| WO | WO 2000/069521 | 11/2000 |
| WO | WO 2000/072905 | 12/2000 |
| WO | WO 2000/074758 | 12/2000 |
| WO | WO 2000/076568 | 12/2000 |
| WO | WO 2000/078384 | 12/2000 |
| WO | WO 2001/062326 | 8/2001 |
| WO | WO 2001/095965 | 12/2001 |
| WO | WO 2001/097892 | 12/2001 |
| WO | WO 2001/097893 | 12/2001 |
| WO | WO 2002/038221 | 5/2002 |
| WO | WO 2002/045784 | 6/2002 |
| WO | WO 03/082406 A2 | 10/2003 |
| WO | WO 2003/090827 | 11/2003 |
| WO | WO 2003/105921 | 12/2003 |
| WO | WO 2004/022146 | 3/2004 |
| WO | WO 2004/041342 | 5/2004 |
| WO | WO 2004/073778 | 9/2004 |
| WO | WO 2004/078230 | 9/2004 |
| WO | WO 2005/053781 | 6/2005 |
| WO | WO 2005/063326 | 7/2005 |
| WO | WO 2005/063328 | 7/2005 |
| WO | WO 2005/086943 | 9/2005 |
| WO | WO 2005/099801 | 10/2005 |
| WO | WO 2005/110220 | 11/2005 |
| WO | WO 2005/118040 | 12/2005 |
| WO | PCT/AU2006/000031 | 1/2006 |
| WO | PCT/AU2006/000417 | 3/2006 |
| WO | PCT/AU2006/000770 | 6/2006 |
| WO | WO 2006/069415 | 7/2006 |
| WO | WO 2006/074513 | 7/2006 |
| WO | WO 2006/074516 | 7/2006 |
| WO | WO 2006/099658 | 9/2006 |
| WO | WO 2006/113321 A2 | 10/2006 |
| WO | WO 2006/130903 | 12/2006 |
| WO | WO 2007/009182 | 1/2007 |
| WO | WO 2007/041751 | 4/2007 |
| WO | WO 2007/041786 | 4/2007 |
| WO | WO 2007/048174 | 5/2007 |
| WO | WO 2007/053878 | 5/2007 |
| WO | WO 2007/115153 A2 | 10/2007 |
| WO | WO 2007/120355 A2 | 10/2007 |
| WO | PCT/AU2007/001936 | 12/2007 |
| WO | WO 2007/143772 | 12/2007 |
| WO | WO 2007/145534 | 12/2007 |
| WO | WO 2008/011682 | 1/2008 |
| WO | WO 2008/011683 | 1/2008 |
| WO | WO 2008/040050 | 4/2008 |
| WO | WO 2008/063923 A2 | 5/2008 |
| WO | WO 2008/070929 | 6/2008 |
| WO | WO 2009/108994 | 9/2009 |
| WO | WO 2009/109004 | 9/2009 |
| WO | WO 2010/009877 | 1/2010 |
| WO | WO 2010/028425 | 3/2010 |

OTHER PUBLICATIONS

Chinese Office Action and English translation thereof mailed Nov. 6, 2020 in corresponding CN Application 201611072310.X (15 pages).
Summons to attend oral proceedings pursuant to Rule 115(1) EPC with Annex mailed Dec. 11, 2020 in related EP Application 09812518.0 (5 pages).
Chinese Notification of the Third Office Action and English translation thereof mailed May 12, 2020 in corresponding Chinese application 201611072310.X.
NZ Further Examination Report mailed Jun. 17, 2020 in related NZ application 754381.
Chinese Notification of the Second Office Action and English translation thereof mailed Sep. 5, 2019 in corresponding Chinese application 201611072310.X.
NZ First Examination Report mailed Jun. 14, 2019 in related NZ application 754381.
International Preliminary Report on Patentability mailed Jul. 8, 2010 in corresponding PCT application PCT/AU2009/000262.
EP Communication pursuant to Article 94(3) EPC mailed Apr. 14, 2019 in corresponding EP application 097168058.
NZ First Examination Report mailed Mar. 11, 2019 in corresponding AU application 751320.
NZ Further Examination Report mailed May 16, 2019 in corresponding AU application 751320.
EP Communication pursuant to Article 94(3) EPC mailed Mar. 13, 2019 in related EP Application 09812518.0.
CN Examination Decision on Request for Reexamination and English translation thereof mailed Apr. 3, 2019 in corresponding CN Application 201510114255.5.

(56) References Cited

OTHER PUBLICATIONS

A Further Examination Report issued in corresponding New Zealand Application No. 735524 dated Dec. 6, 2018, (3 pages).
A Further Examination Report issued in corresponding New Zealand Application No. 735524 dated Feb. 12, 2019, (2 pages).
An Office Action dated Jan. 29, 2019 in corresponding CN Application No. 201611072310X and translation thereof, (9 pages).
U.S. Appl. No. 10/385,701, filed Aug. 2003, Berthon-Jones et al.
U.S. Appl. No. 10/533,928, filed Jul. 2005, Berthon-Jones.
U.S. Appl. No. 10/584,711, filed Dec. 2004, Davidson.
U.S. Appl. No. 10/655,622, filed Sep. 2003, Lithgow.
U.S. Appl. No. 10/781,929, filed Jan. 2008, Gunaratnam et al.
U.S. Appl. No. 10/871,929, filed Feb. 2004, Surjaatmadja.
U.S. Appl. No. 11/080,446, filed Jul. 2005, Ging et al.
U.S. Appl. No. 11/447,295, filed Jun. 2006, Lubke et al.
U.S. Appl. No. 11/474,415, filed Jun. 2006, Davidson et al.
U.S. Appl. No. 11/491,016, filed Feb. 2007, Kwok et al.
U.S. Appl. No. 11/703,082, filed Feb. 2007, Davidson.
U.S. Appl. No. 11/878,932, filed Jul. 2007, Veliss et al.
U.S. Appl. No. 11/878,933, filed Jul. 2007, Veliss et al.
U.S. Appl. No. 12/081,696, filed Apr. 2008, Davidson et al.
U.S. Appl. No. 12/085,191, filed May 2008, Kwok et al.
U.S. Appl. No. 12/219,852, filed Jul. 2008, Guney et al.
U.S. Appl. No. 12/309,696, filed Jan. 2009, Kwok et al.
U.S. Appl. No. 12/382,517, filed Mar. 2009, Lithgow.
U.S. Appl. No. 12/448,250, filed Jun. 2009, Veliss et al.
U.S. Appl. No. 12/461,448, filed Aug. 2009, Berthon-Jones.
U.S. Appl. No. 12/478,537, filed Jun. 2009, Kooij et al.
U.S. Appl. No. 12/656,466, filed Jan. 2010, Biener et al.
U.S. Appl. No. 12/700,878, filed Feb. 2010, Davidson et al.
U.S. Appl. No. 60/424,686, filed Nov. 2002, Lithgow.
U.S. Appl. No. 60/483,622, filed Jul. 2003, Kwok et al.
U.S. Appl. No. 60/533,214, filed Dec. 2003, Drew.
U.S. Appl. No. 60/634,802, filed Dec. 2004, Chandran.
U.S. Appl. No. 60/645,672, filed Jan. 2005, Chandran.
U.S. Appl. No. 60/795,615, filed Apr. 2006, Judson et al.
U.S. Appl. No. 60/833,841, filed Jul. 2006, Veliss.
U.S. Appl. No. 60/835,442, filed Aug. 2006, Selvarajan et al.
U.S. Appl. No. 60/852,649, filed Oct. 2006, Selvarajan et al.
U.S. Appl. No. 60/874,968, filed Dec. 2006, Kwok et al.
U.S. Appl. No. 60/907,856, filed Apr. 2007, Davidson et al.
U.S. Appl. No. 60/924,241, filed May 2007, Kwok et al.
U.S. Appl. No. 60/929,393, filed Jun. 2007, Kwok et al.
U.S. Appl. No. 60/935,179, filed Jul. 2007, Guney et al.
U.S. Appl. No. 60/935,336, filed Aug. 2007, Davidson et al.
U.S. Appl. No. 60/996,160, filed Nov. 2007, Guney et al.
U.S. Appl. No. 61/006,409, filed Jan. 2008, Guney et al.
U.S. Appl. No. 61/064,818, filed Mar. 2008, Guney et al.
U.S. Appl. No. 61/071,512, filed May 2008, Guney et al.
U.S. Appl. No. 61/213,326, filed May 2009, Dravitzki et al.
U.S. Appl. No. 61/222,711, filed Jul. 2009, Dravitzki et al.
U.S. Appl. No. 61/263,175, filed Nov. 2009, Dravitzki et al.
U.S. Appl. No. 61/272,162, filed Aug. 2009, Dravitzki et al.
U.S. Appl. No. 61/272,250, filed Sep. 2009, Dravitzki et al.
A Notification of Reexamination issued in corresponding Chinese Application No. 2015101142555 dated Aug. 29, 2018, with English translation, (38 pages) A Further Examination Report issued in corresponding New Zealand Application No. 735524 dated Oct. 17, 2018, (2 pages) An Examination Report issued in corresponding European Application No. 09716805.8 dated Aug. 31, 2018, (8 pages) Further Examination Report dated Oct. 20, 2014 issued in corresponding New Zealand Application No. 608162 (2 pages). International Search Report issued in Appln. No PCT/AU2009/000262 (Jun. 9, 2009). First Examination Report dated Oct. 1, 2014 issued in corresponding New Zealand Application No. 700228 (2 pages) Notification of the Fourth Office Action dated Jul. 25, 2014 issued in corresponding Chinese Application No. 200980107829.9 with English translation (17 pages). Patent Examination Report No. 1 issued Feb. 28, 2013 in corresponding Australian Patent Application No. 2009221639 (3 pages total). "Ear Loop Face Mask".

A Further Examination Report issued in corresponding New Zealand Application No. 735524 dated Oct. 17, 2018, (2 pages).
An Examination Report issued in corresponding European Application No. 09716805.8 dated Aug. 31, 2018, (8 pages).
Further Examination Report dated Oct. 20, 2014 issued in corresponding New Zealand Application No. 608162 (2 pages).
International Search Report issued in Appln. No PCT/AU2009/000262 (Jun. 9, 2009).
First Examination Report dated Oct. 1, 2014 issued in corresponding New Zealand Application No. 700228 (2 pages).
Notification of the Fourth Office Action dated Jul. 25, 2014 issued in corresponding Chinese Application No. 200980107829.9 with English translation (17 pages).
Patent Examination Report No. 1 issued Feb. 28, 2013 in corresponding Australian Patent Application No. 2009221639 (3 pages total).
"Ear Loop Face Mask".
Adam J. Singer MD et al. "The Cyanoacrylate Topical Skin Adhesives," American Journal of Emergency Medicine, vol. 26, 2008, pp. 490-496.
Webster's Third New International Dictionary, 1993, Dictionary definition for adjustable, bendable, and mild steel.
ComfortLite™, Respironics, http://comfortlite.respironics.com.
ComfortLite™ 2, Respironics, http://comfortlite2.respironics.com.
"If You Hate CPAP! You Need CPAP Pro®," ww.cpappro.com.
Webster's New World Dictionary, Third College Edition 1988, definition for engaged and flexible.
EP Supplementary Search Report issued in EP Application 03793493, dated Dec. 2, 2009.
European Search Report filed on Jul. 27, 2009 in EP Application No. 07784697.0.
European Search Report issued in EP 07845378.4, mailed Dec. 1, 2009.
Examination Report filed in New Zealand Application 539836, dated Aug. 25, 2005.
Examiner's Report No. 3 mailed Nov. 18, 2009 in New Zealand Application No. 2003275762.
Extended European Search Report dated Mar. 19, 2009 in European Application No. EP 08161249.
Extended European Search Report Mailed Sep. 3, 2009 in corresponding EP Application No. 09161984.1.
Extended European Search Report. Application No. EP 08154854, dated Nov. 27, 2008.
Fisher and Paykel Col.—Product Family—http://www.fphcare.com/osa/products.asp/.
Hans Rudolph, Inc.—Mask Products—http://www.rudolphc.com/products.php?category=MASKS.
International Preliminary Report on Patentability for PCT/AU2004/001832, dated Jul. 3, 2006.
International Search Report filed in PCT/AU2005/000803, dated Jun. 30, 2005.
International Search Report filed in PCT/AU2006/000770, dated Aug. 3, 2006.
International Search Report for PCT/AU2007/001052, dated Oct. 9, 2007.
International Search Report for PCT/AU2007/001051, dated Nov. 5, 2007.
International Search Report for PCT/AU2004/001832, dated Mar. 24, 2005.
International Search Report for PCT/AU2007/001936, dated Mar. 4, 2008.
Joel W. Beam, "Tissue Adhesives for Simple Traumatic Lacerations," Journal of Athletic Training, 2008, vol. 43, No. 2, pp. 222-224.
Merriam-Webster Online Dictionary definition of moveable from the 14th century.
Office Action mailed Dec. 22, 2009 in European Appln. No. 04802133.1.
Office Action issued in Japanese Application No. 2007-513621 (Aug. 24, 2010) with English translation.
ResMed Co.—Mask Products—http://resmed.com/portal/site/ResMedUS/index.jsp?. . . .

(56) References Cited

OTHER PUBLICATIONS

Respironics Co.—Mask Family—http:/masksfamily.respironics.com/.
SNAPP Nasal Interface, Tiara Medical Systems, Inc.—http://www.tiaramed.com/asp_shops/shopdisplayproducts.asp?id=109&cat=SNAPP%2A+Nasal+Interface.
Subbu Venkatraman et al., "Review Skin Adhesives and Skin Adhesion 1. Transdermal Drug Delivery Systems," Biomaterials, vol. 19, 1998, pp. 1119-1136.
Supplementary European Search Report mailed Sep. 8, 2009 in European Appln. No. 04802133.1.
Supplementary European Search Report mailed Dec. 18, 2009 in European Application No. 03810331.3.
Unsolicited email from Elson Silva, PhD, dated Mar. 28, 2008, "Requesting IDS of U.S. Pat. No. 6,766,817 for patents on fluids moving on porosity by Unsaturated Hydraulic Flow," (email provided in both HTML and plain text format).
International Search Report PCT/AU2003/001163, dated Nov. 4, 2003.
International Search Report PCT/AU2003/001471, dated Feb. 12, 2004.
International Search Report PCT/AU2009/000240, dated May 21, 2009.
International Search Report PCT/AU2009/001144, dated Dec. 18, 2009.
Office Action issued in European Appln. No. 05746824.1 (Mar. 22, 2011).
Patent Examination Report No. 2 issued Feb. 27, 2014 in corresponding Australian Patent Application No. 2009221639 . . . .
Further Examination Report issued Jun. 30, 2014 in corresponding New Zealand Application No. 608162 . . . .
Notice of Allowance issued in corresponding Japanese Patent Application No. 2010-548988 on Mar. 3, 2014.
Third Office Action issued in corresponding Chinese Application No. 200980107829.9 on Nov. 26, 2013 with English-language translation thereof.
Office Action in corresponding Chinese Application No. 200980107829.9 issued on May 6, 2013 with English-language translation.
First Examination Report issued in a corresponding New Zealand Application No. 608162 on Mar. 15, 2013.
Office Action issued in a corresponding Japanese Application No. 2010-548988 on Apr. 23, 2013 with English-language translation.
Office Action issued in a related Chinese Application No. 200980107829.9 (Jun. 11, 2012) with English translation thereof.
Patent Examination Report No. 2 issued Nov. 24, 2016 in a corresponding Australian Application No. 2015200781 (3 pages).
Further Examination Report issued in related New Zealand Patent Appln. No. 615630, dated Mar. 20, 2015 (2 pages).
Further Examination Report issued in related New Zealand Patent Appln. No. 615630, dated Apr. 10, 2015 (2 pages).
Patent Examination Report No. 3, issued Jun. 3, 2015, in a related Australian Application No. 2009291491 (3 pages).
Decision of Rejection issued Dec. 1, 2014 in corresponding Chinese Patent Application Publication No. CN 1681553 A with English-language translation thereof.
Notice of Allowance issued Oct. 7, 2016, in a related Japanese Application No. 2015-109892 (3 pages).
Examination Decision of the Patent Examination Board issued Aug. 30, 2016, in a corresponding Chinese Application No. 200980107829.9 (11 pages) and an English translation thereof (12 pages).
First Office Action issued Sep. 5, 2016, in a related Chinese application No. 201510141153.2 (11 pages), and an English translation thereof (13 pages).
First Office Action issued Jul. 28, 2016 in a corresponding Chinese Application No. 201510114255.5 (10 pages), and an English translation thereof (10 pages).
Requisition by the Examiner issued May 29, 2015, in a related Canadian Application No. 2,735,986 (4 pages).
Office Action issued Jun. 8, 2015 in a related Japanese Patent Application No. 2014-109892 (3 pages) and English translation thereof (4 pages).
Communication including extended European Search Report issued Aug. 26, 2015, in a related European Application No. 09 81 258.0 (11 pages).
First Examination Report issued Apr. 5, 2016, in a corresponding New Zealand Application No. 717325 (2 pages).
Patent Examination Report No. 1 issued Mar. 11, 2016 in a corresponding Australian Application No. 2015200781 (5 pages).
Notification of Reexamination issued Feb. 23, 2016 in a corresponding Chinese Application No. 200980107829.9 (7 pages) and English translation thereof (8 pages).
Deadline for Counterstatement issued Jan. 5, 2016 in a related New Zealand Application No. 615630 (1 page), Amended Notice of Opposition filed Nov. 27, 2015 (both markup and clean copies) (6 pages), and Statement of the Case filed Nov. 27, 2015 (9 pages).
Notice of Opposition to Grant of Patent filed Sep. 29, 2015 in a related New Zealand Application No. 615630 (5 pages).
A Requisition by the Examiner issued Dec. 14, 2017, in a related Canadian Patent Application No. 2,941,584 (3 pages).
A Third Examination Report dated Jan. 16, 2018, in a related Australian Patent Application No. 2015238868 (4 pages), citing U.S. Patent Publication No. US 2006/0096598.
A First Examination Report issued Jul. 12, 2016, in a related New Zealand Patent Application No. 719072 (3 pages).
A First Examination Report issued Sep. 22, 2017, in a corresponding New Zealand Patent Application No. 733524 (2 pages), citing European Patent Application No. EP 2 259 828 (the publication of this application, WO 2009/109004, was previously cited in this application).
An Office Action mailed Oct. 23, 2017, in a related Japanese Patent Application No. 2016-216279 (2 pages), and an English translation thereof (3 pages), citing French Patent Application No. FR 2 823 122 (14 pages with abstract), Japanese Patent Application No. JP 2002-028240 (26 pages with abstract), Japanese Patent Application No. JP 2006-505373 (81 pages with abstract), Japanese Patent Application No. JP 2008-626393 (30 pages with abstract), Japanese Patent Application No. JP 2009-520579 (36 pages with abstract), and Japanese Patent Application No. JP 2011-512968 (25 pages with abstract).
A Decision of Rejection issued Aug. 8, 2017, in a corresponding Chinese Application No. 201510114255.5 (18 pages), and an English translation thereof (21 pages).
A Non-Final Office Action issued Sep. 13, 2017, in related U.S. Appl. No. 14/524,097 (58 pages), citing U.S. Patent Publication No. US 2004/0133958 (Darnell).
A Further Examination Report issued Jun. 19, 2017 in a corresponding New Zealand Application No. 717325 (2 pages).
A Communication Pursuant to Article 94(3) EPC issued Jun. 20, 2017, in a corresponding European Application No. 09 716 805.8 (8 pages).
An Office Action issued Jun. 13, 2017, in a related Canadian Application No. 2,941,584 (3 pages).
A Second Office Action issued Feb. 13, 2017 in a corresponding Chinese Application No. 2015101142555 (16 pages), and an English translation thereof (19 pages).
Examination Report No. 1 issued Jan. 20, 2017, in a related Australian Application No. 2015238868 (8 pages).
Extended European Search Report issued Jun. 30, 2022, in related European Application No. EP 21217202.7, 7 pages.
Office Action issued Aug. 2, 2022, in related U.S. Appl. No. 16/288,495, 15 pages.
Extended EP Search Report mailed Nov. 18, 2021 in corresponding EP application 21174225.9 (19 pages).
Office Action mailed Mar. 29, 2022 in related U.S. Appl. No. 16/288,495 (46 pages).

\* cited by examiner

INTERFACE INCLUDING A FOAM CUSHIONING ELEMENT

CROSS-REFERENCE TO APPLICATION

This application is a continuation of U.S. patent application Ser. No. 15/987,734, filed May 23, 2018, now allowed, which is a continuation of U.S. patent application Ser. No. 12/736,030, filed Sep. 2, 2010, issued as U.S. Pat. No. 9,987,450, which was the U.S. national phase of International Application No. PCT/AU2009/000262, filed Mar. 4, 2009, which designated the U.S. and claims the benefit of Australian Provisional Application No. AU 2008901056, filed Mar. 4, 2008, each of which is hereby incorporated herein by reference in its entirety.

FIELD OF THE INVENTION

The present invention relates to an interface between a human and a piece of equipment, for example a mask, that includes a foam-based cushioning element.

BACKGROUND OF THE INVENTION

In a number of fields, such as respiratory therapy, apparatus for delivery of therapy includes a more rigid component defining a structure and a soft, cushioning component positioned between the patient and the rigid component.

In the case of a respiratory device, the more rigid component may be a mask frame defining a nose-receiving chamber. The mask frame may include a flange around its periphery. The cushioning component may be glued to the flange. See U.S. Patent Application Publication US 2003/0168063.

The cushioning component may form an air tight seal with the skin of the patient in some forms of respiratory therapy. In other devices, for example headphones, it may not be necessary for an air tight seal to be formed.

Other known masks that include foam cushioning elements include the following Fisher and Paykel masks: ACLAIM mask, FLEX-FIT 405, FLEX-FIT 407, and FLEX-FIT 431.

SUMMARY OF THE INVENTION

A first aspect of the invention is to provide a patient interface with a foam cushioning element.

Another aspect of the invention is to provide a patient interface with a removable foam cushioning element.

Another aspect of the invention is to provide a patient interface system with at least two different types of removably replaceable cushioning elements.

Another aspect of the invention is to include a cushioning element having portion adapted for engagement with a more rigid component.

Another aspect of the invention is to provide a respiratory mask assembly including a frame and a cushioning element wherein the cushioning element includes a foam-based interfacing portion and a clip portion adapted for removable engagement with the frame portion.

Another aspect of the invention is to provide a support structure for a cushioning element that supports the cushioning element on one side and allows movement on another side.

Another aspect of the invention relates to a cushion for a respiratory mask including a clip portion and an interfacing portion wherein the interfacing portion is constructed from a foam material and the clip portion is narrower than the interfacing portion.

Another aspect of the invention relates to a respiratory mask assembly including a frame having a channel and a cushioning element including a clip portion adapted for interference seal and retention in the channel. The cushioning element includes an interfacing portion constructed from foam and having a wider width than the clip portion.

Another aspect of the invention relates to a respiratory mask assembly including a frame having a channel and a removably replaceable interfacing structure including a clip portion adapted for interference seal and retention in the channel. The interfacing structure includes a cushion component constructed from foam.

Another aspect of the invention relates to a mask system including a common frame and at least a first cushion constructed from foam and a second cushion constructed from silicone. The first and second cushions are each structured to removably attach to the frame.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 4b shows a bottom view of the cushioning element of FIG. 4a;

FIG. 4c shows a top view of the cushioning element of FIG. 4a;

FIG. 4d shows a side view of the cushioning element of FIG. 4a;

FIG. 4e shows a frame contacting side of the cushioning element of FIG. 4a;

FIG. 4f shows a patient contacting side isometric view of the cushioning element of FIG. 4a;

FIG. 4g shows a frame contacting side isometric view of the cushioning element of FIG. 4a;

FIG. 5b is an isometric view of the cushioning element shown in FIG. 5a;

FIG. 6b shows a detail in the nasal bridge region of the mask of FIG. 6a;

FIG. 7b is a cross-section along line 7b-7b of FIG. 7a;

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

Interconnection of Cushioning Element and Apparatus

In accordance with an embodiment of the present invention, a removable interconnectable cushioning element (also referred to as a cushion element or cushion) is provided. The cushioning element preferably includes a soft resilient foam interfacing portion for contacting a human. The cushioning element is constructed and arranged for removable interconnection with the rest of the apparatus, for example a respiratory mask.

The ability to removably connect the cushioning element enables one to replace the cushioning element should it become soiled and/or uncomfortable. It also facilitates trial of different forms of cushioning element. One form of cushioning element, for example a foam-based cushioning element, may be used as a form of "training" system to allow a person to become accustomed to the sensation of wearing and using a mask. A foam-cushion based mask may provide an initially more appealing and comfortable surface for a new patient than a gel or silicone-based cushion. The patient may subsequently switch from the foam-based cushion to a silicone or gel based cushion. In this way, the patient may be more likely to adhere to therapy because they are used to the very soft comfortable feeling of foam.

When applied to respiratory equipment, the cushioning element is adapted for connection with a mask frame. In use, an air-tight seal is formed between the cushioning element and the frame. This arrangement could be used for both nasal and full-face masks.

Figure 1:
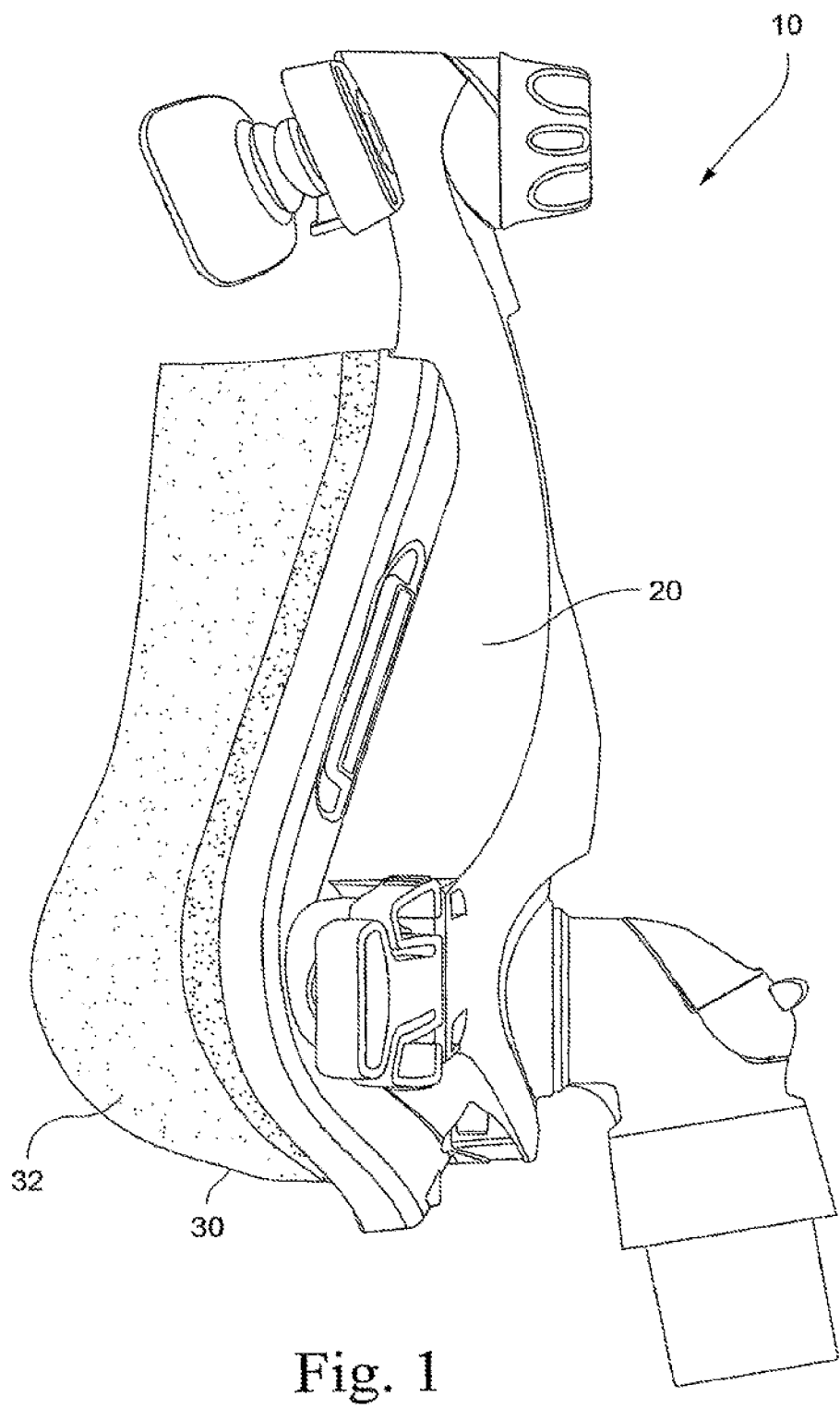
FIG. 1 shows a side view of a mask assembly including a foam cushioning element according to an embodiment of the invention.

For example, FIG. 1 illustrates a mask 10 including a mask frame 20 and a foam-based cushioning element 30 provided to the mask frame 20. As illustrated, the foam-based cushioning element 30 provides a foam interfacing portion 32 adapted to contact the patient's face in use. In this embodiment, the foam-based cushioning element 30 is adapted for use with an existing mask (e.g., ResMed's Mirage Quattro mask), which allows the patient to switch from the foam-based cushioning element 30 to the mask's existing silicone-based cushion if desired.

Dual Foam Layers

In one form of device in accordance with an embodiment of the invention, the foam-based cushioning element has two layers, i.e., an interfacing portion and a clip portion.

In an embodiment, the interfacing portion or cushion is constructed from a soft unskinned resilient viscoelastic polyurethane foam. Such a foam is disclosed in PCT Publication Nos. WO 2008/011682, published Jan. 31, 2008, and WO 2008/070929, published Jun. 19, 2008, each of which is incorporated herein by reference in its entirety. In one form, the resilient foam may be formed by a known method such as die cutting.

FIGS. 4a to 4g show a foam-based cushioning element 230 according to an embodiment of the invention. As illustrated, the cushioning element 230 includes an interfacing portion (or face-contacting portion) 232 and a clip portion 234 provided to the interfacing portion 232. In this embodiment, the clip portion 234 is adapted for an interference fit with a mask frame, and the width of the clip portion 234 is narrower than the width of the interfacing portion 232 (e.g., see FIGS. 4e and 4g).

In the illustrated embodiment, both an inside surface and an outside surface of the foam interfacing portion 232 are die cut. This typically results in straight cut edges, much like a kitchen sponge. The cushion may therefore have a square cross section.

In an embodiment, the clip portion of the cushioning element may be constructed from a more rigid foam than the interfacing portion. For example, the clip portion may be formed from nitrogen blown polyethylene, or some other clean, biocompatible foam having a fine cell-structure. Alternatively, the clip portion could be made from some other polymer or rubber. In an embodiment, the clip portion is adapted to form a cushion-to-frame engagement mechanism and to form a structural support for the interfacing portion.

The two layers (i.e., the interfacing portion and the clip portion) may be adhered to one another using polyurethane hot melt glue. This arrangement provides a one piece cushioning element with an interfacing portion adapted to engage the patient's face and a clip portion adapted to interface with the mask frame.

Cushion-to-Frame Engagement Mechanisms

According to an aspect of the invention, the cushion-to-frame engagement and connection mechanism provided by the clip portion may include a channel-type engagement or rib-type engagement.

Figure 2:
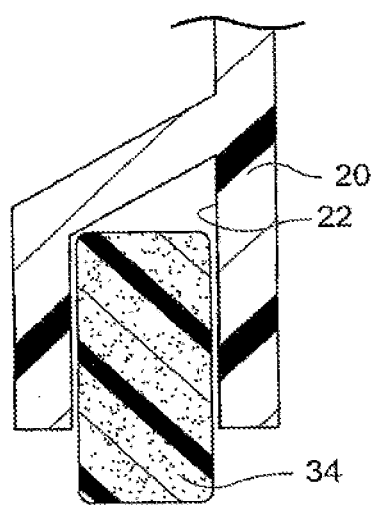
FIG. 2 shows a schematic diagram of a channel of a portion of a mask frame and a clip portion of a cushioning element retained by an interference fit according to an embodiment of the invention.

As shown in FIG. 2, the channel-type engagement includes a foam clip portion 34 that is adapted to be received within the channel 22 of a mask frame 20 with an interference fit. The foam clip portion 34 extends around the entire perimeter of the cushioning element so as to form an air-tight seal and retention with the mask frame.

Figure 3A:
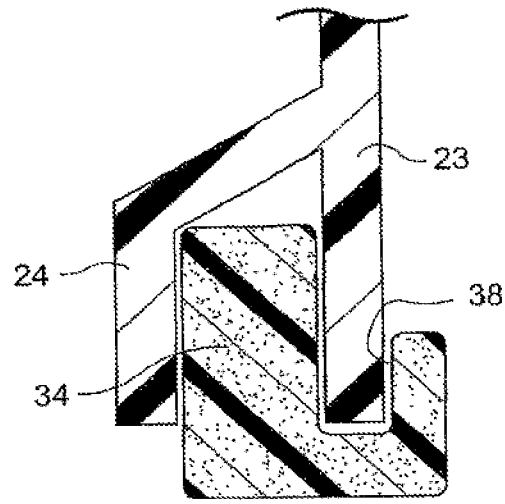
FIGS. 3a, 3b, and 3c show a range of rib engagement fitting arrangements between a mask frame and a clip portion of a cushioning element according to embodiments of the invention.
Figure 3B:
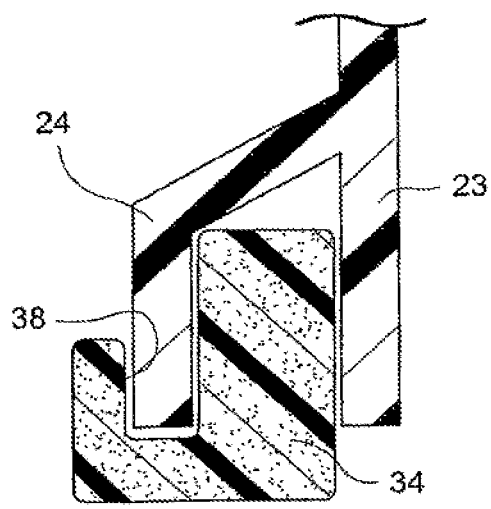
Figure 3C:
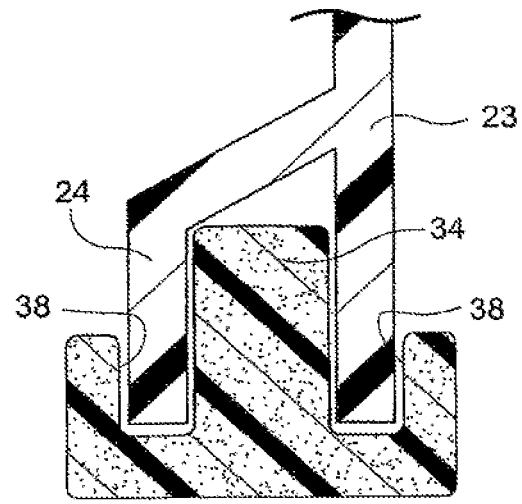

As shown in FIGS. 3a to 3c, the rib-type engagement includes a foam clip portion 34 with one or more slots 38 to receive inner and/or outer ribs 23, 24 of the mask frame 20. For example, the slot to rib engagement may provide an inner frame rib engagement (see FIG. 3a), an outer frame rib engagement (see FIG. 3b), or an inner and outer frame rib engagement (see FIG. 3c). This arrangement provides a broader base of support for the sealing foam.

Figure 5A:
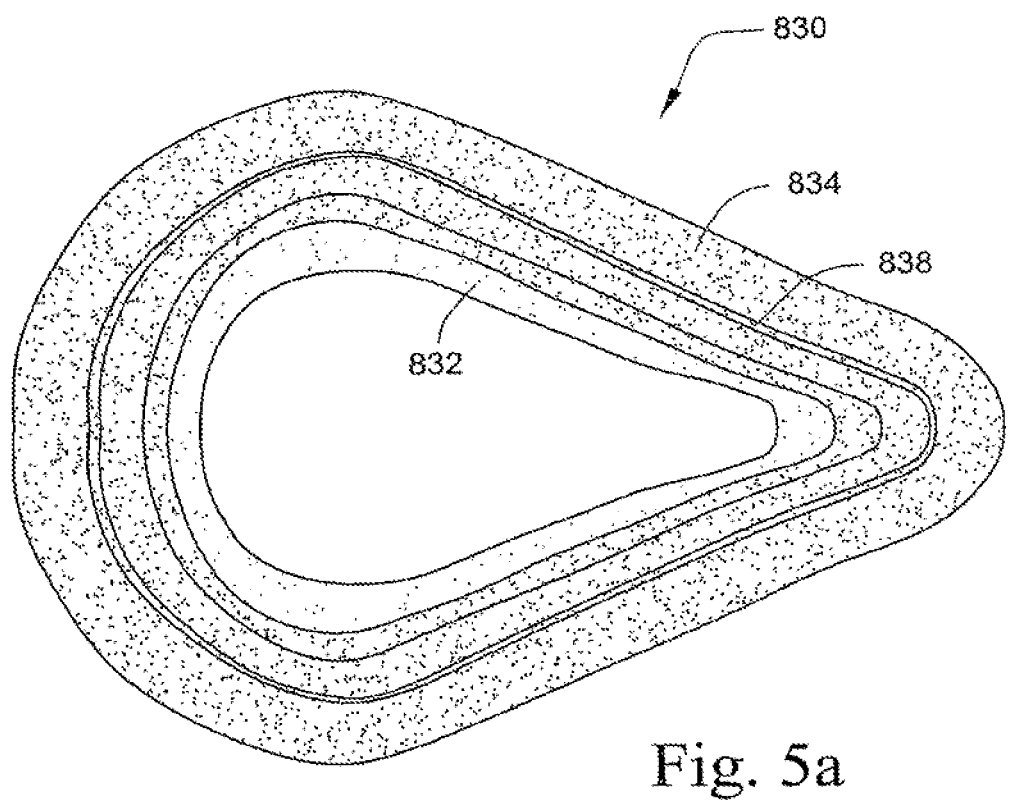
FIG. 5a is a plan view showing a die cut cushioning element wherein the clip portion includes a slot for engagement with the frame according to an embodiment of the invention.
Figure 5B:
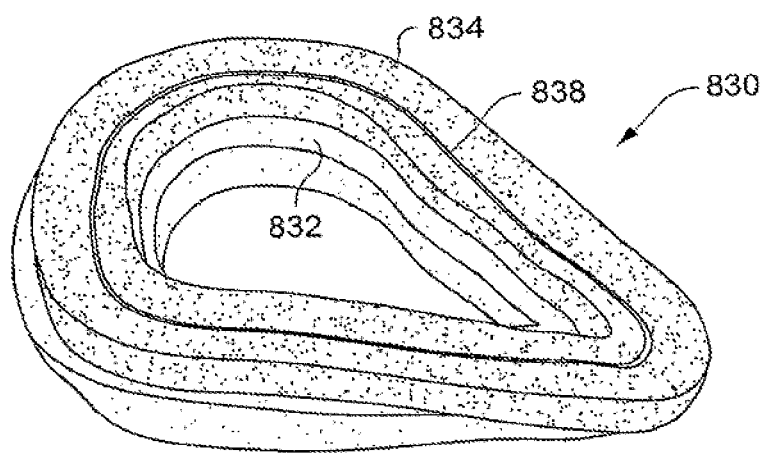
Figure 5C:
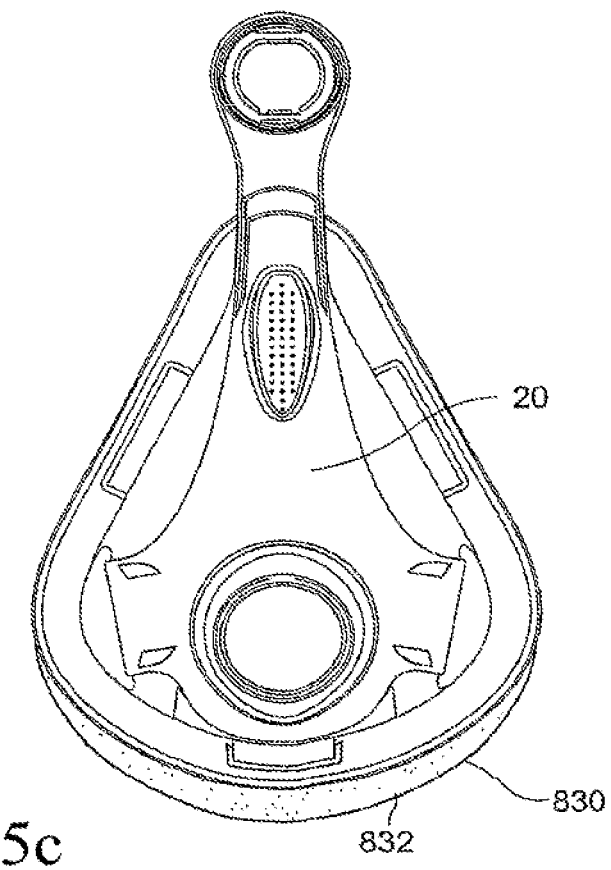
FIG. 5c is an assembly view of the cushioning element shown in FIG. 5a with a mask frame.

FIGS. 5a and 5b illustrate a foam-based cushioning element 830 including a foam interfacing portion 832 and a clip portion 834, and FIG. 5c illustrates the cushioning element 830 provided to a mask frame 20. As shown in FIGS. 5a and 5b, the clip portion 834 includes a slot 838 adapted to receive a rib of the mask frame 20. Also, providing a wider clip portion 834 allows more stiffness and structural integrity to be provided to the clip portion, making the clip portion easier to assemble to the mask frame.

When structured to form an interference fit with the mask frame, the clip portion may have the following properties: appropriate rigidity (e.g., less than that of the frame and in one form more rigid than the foam interfacing portion); non-porous; and/or low compression set (the amount of deformation expressed as a percentage of original dimensions) which a material retains after compressive stress is released (in this way, the clip portion maintains its retention force during its usage life).

Interfacing Portion Support Structure

In accordance with an embodiment of the invention, a range of different arrangements of clip portions and foam interfacing portions may be provided. For example, the width of the clip portion may match the interfacing portion, the width of the clip portion may be less than the width of the interfacing portion, or the width of the clip portion may be greater than the width of the interfacing portion.

When the width of the clip portion is less than the width of the interfacing portion, the clip portion and interfacing portion may be arranged such that (i) the outer perimeter of the clip portion and interfacing portion align (hides hardness of clip portion and provides desired freedom of movement in the interfacing portion), (ii) the inner perimeter of the clip portion and the interfacing portion align, or (iii) neither the inner or outer perimeter of the clip portion and the interfacing portion align.

Similarly, when the width of the clip portion is greater than the width of the interfacing portion, the clip portion and interfacing portion may be arranged such that (i) the outer perimeter of the clip portion and interfacing portion align, (ii) the inner perimeter of the clip portion and interfacing portion align, or (iii) neither the inner or outer perimeter of the clip portion and the interfacing portion align.

In these different configurations with different relative widths, the clip portion provides different forms of support of the interfacing portion.

When the width of the clip portion is less than the width of the interfacing portion and the outer perimeter of the clip portion aligns with the interfacing portion, the interfacing portion is more free to flex in regions not having a clip portion next to it than in regions having a clip portion adjacent to it. For example, where the interfacing portion overhangs the clip portion, that overhanging region of the interfacing portion has more freedom to move. This arrangement can be more comfortable and more able to adapt to different geometries of a person, and provide the correct vectors to seal the interfacing portion against the face.

When used as part of a respiratory mask, it may be preferable that the inner portion of the interfacing portion overhang the clip portion. In this arrangement in use, the face of the patient may engage with an unsupported inner edge of the softer interfacing portion causing it to bend and conform to the individual patient's shape.

Figure 4A:
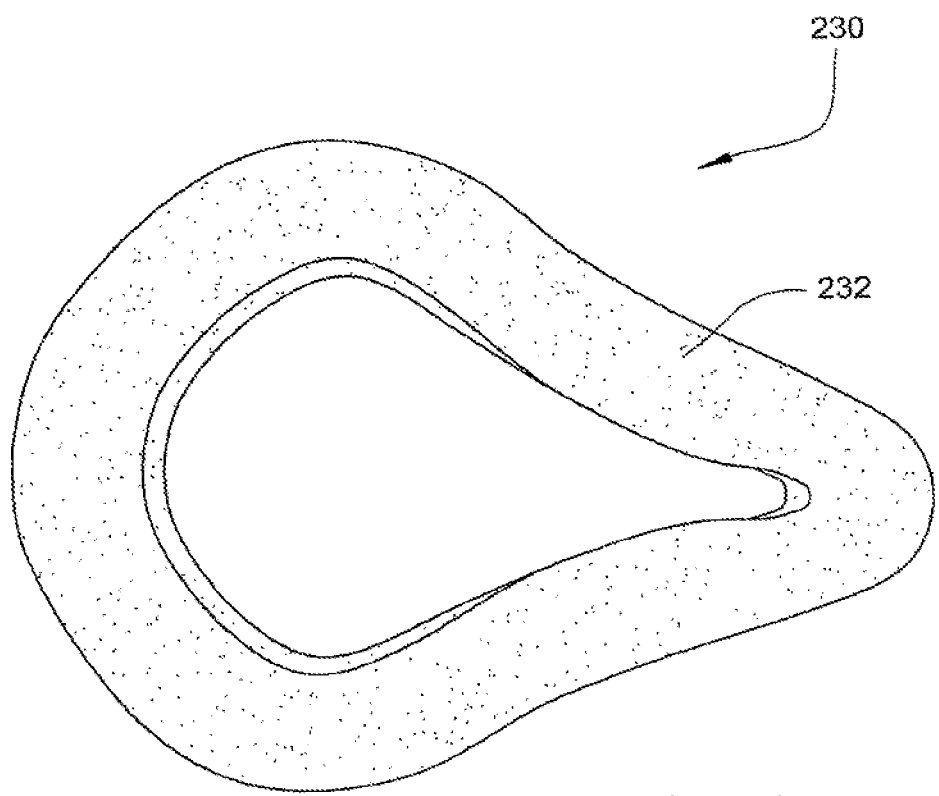
FIG. 4a shows a patient contacting side of a cushioning element according to an embodiment of the invention.
Figure 4B:
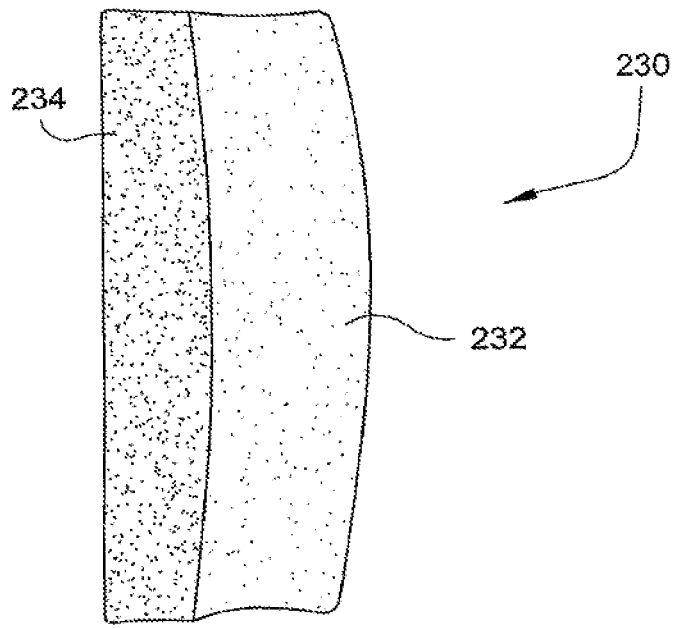
Figure 4C:
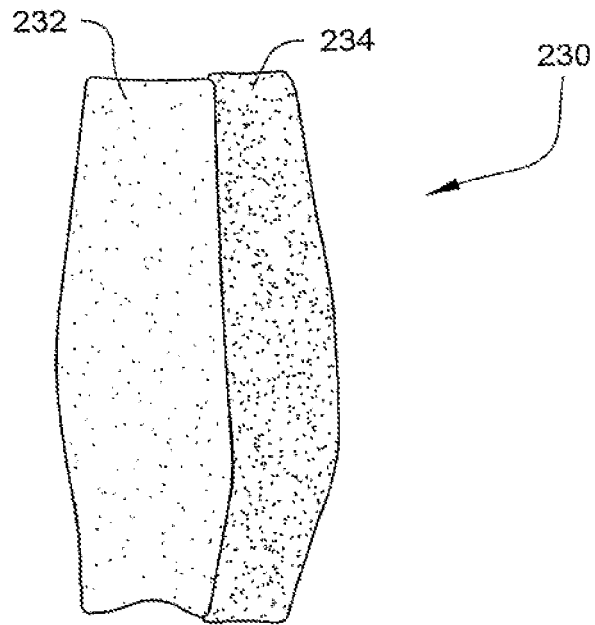
Figure 4D:
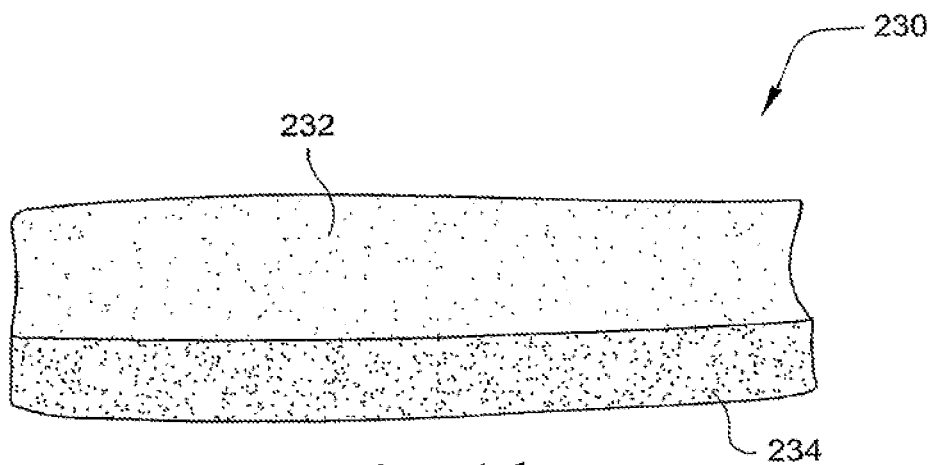
Figure 4E:
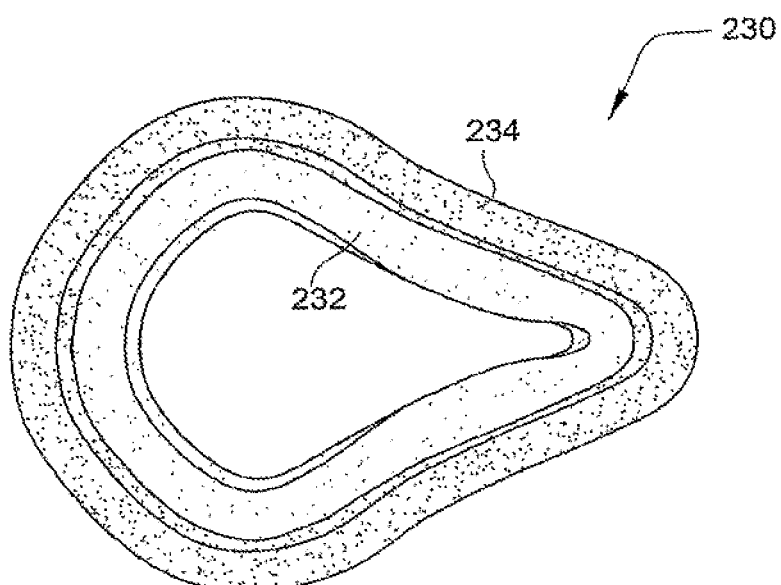
Figure 4F:
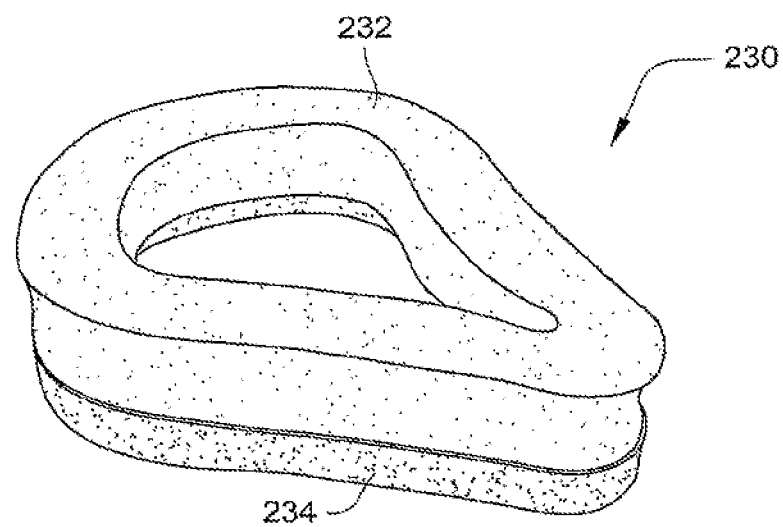
Figure 4G:
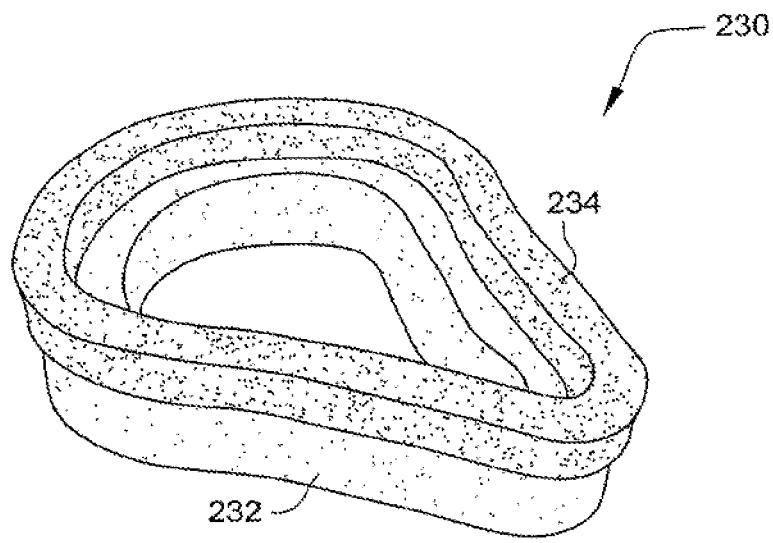
Figure 7A:
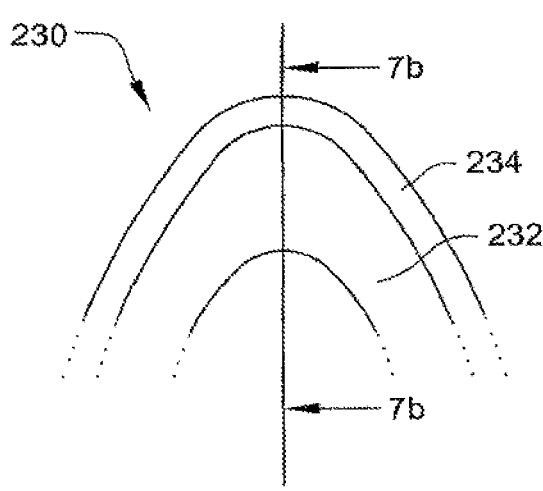
FIG. 7a shows an elevation view detail from the frame side of the cushioning element shown in FIG. 4e.
Figure 7B:
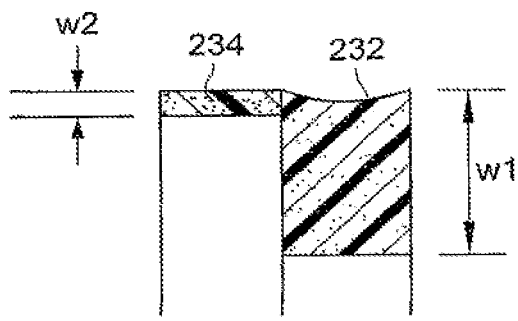
Figure 7C:
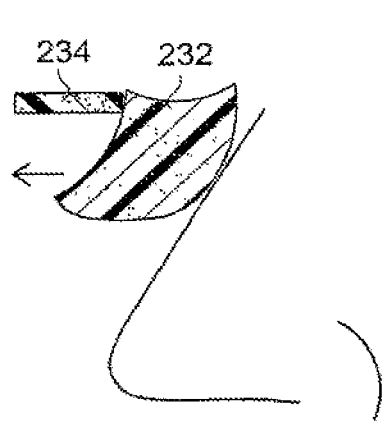
FIG. 7c is a cross-sectional view showing the cushioning element of FIGS. 7a and 7b in use.

FIG. 7a shows an elevation view detail from the frame side of the cushioning element 230 shown in FIG. 4e in a nasal bridge region. As shown in cross-section in FIG. 7b, it is apparent that the width w2 of the clip portion 234 is less than the width w1 of the interfacing portion 232 and that the outer perimeter of the clip portion 234 and the interfacing portion 232 are aligned. An advantage of this arrangement is illustrated in FIG. 7c where in use the nose is able to push the inner perimeter of the interfacing portion 232 in the direction shown by the arrow, in a cantilever manner as well as compressing.

Figure 8:
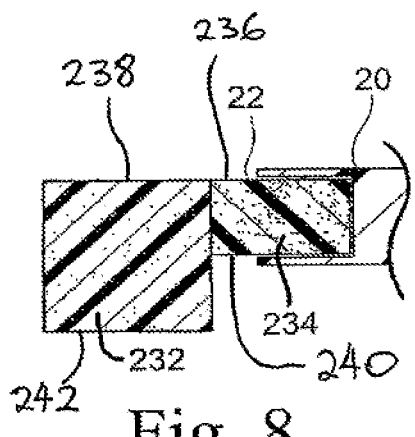
FIG. 8 is a cross-sectional view showing the assembly of the cushioning element of FIGS. 7a and 7b and a frame according to an embodiment of the invention.

FIG. 8 is a cross-section showing the clip portion 234 of the cushioning element 230 received within the channel 22 of a mask frame 20. It can be seen that the width of the clip portion 234 is less than that of the interfacing portion 232, and that the outer perimeter surfaces 236 and 238 respectively of the clip portion 234 and interfacing portion 232 are aligned while the respective inner perimeter surfaces 240, 242 are offset.

Figure 6A:
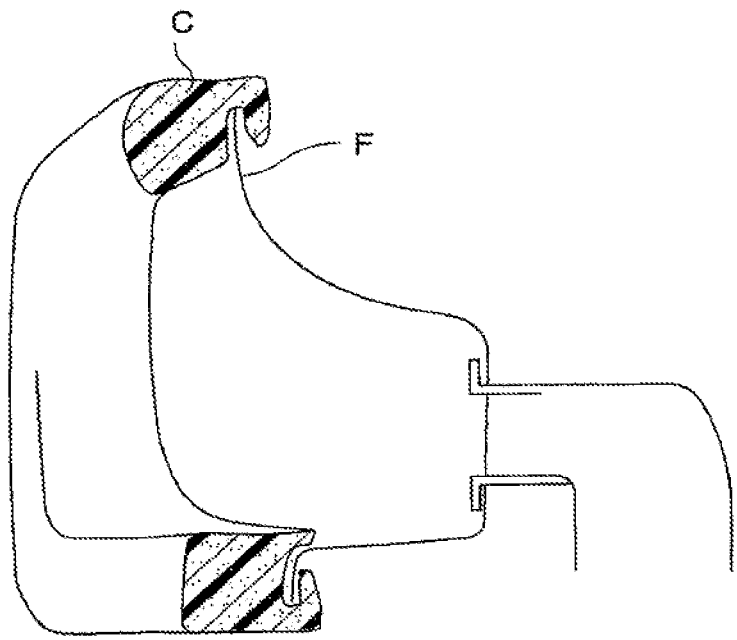
FIG. 6a shows a cross-section from a prior art nasal mask with foam cushion.
Figure 6B:
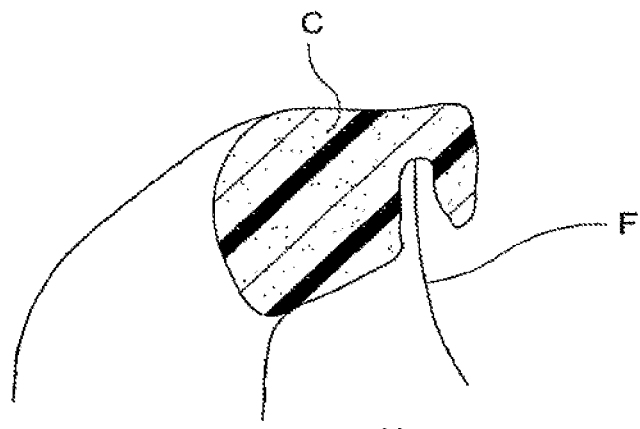

This arrangement is in contrast to prior art cushions (such as the Lifecare mask shown in FIGS. 6a and 6b) where the inner perimeter of the cushion C abuts the frame F, and hence it is not free to move inwardly and can only compress.

In one form, a mask system may be provided that includes at least two different forms of cushioning element chosen from the set of foam-based cushion, silicone-based cushion, and gel-based cushion.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mask system for delivery of respiratory therapy, comprising:
   a common frame at least partially defining a breathing chamber, the common frame being rigid;
   a first cushioning element configured to, in use, form a seal with the patient's skin, the first cushioning element being removably attachable to the common frame, the first cushioning element being a foam-based cushioning element including an interfacing portion comprising a resilient foam arranged to contact the patient's face in use; and
   a second cushioning element configured to, in use, form a seal with the patient's skin, the second cushioning element being removably attachable to the common frame such that the first cushioning element and the second cushioning element are interchangeable on the common frame,
   wherein the second cushioning element is a silicone-based cushioning element comprising a skin contacting surface formed of a silicone material.

2. The mask system of claim 1, wherein each of the first cushioning element and the second cushioning element includes a clip portion for attachment to the common frame.

3. The mask system of claim 2, wherein the clip portion of the first cushioning element has a first side configured for attachment to the common frame and a second side that is attached to the interfacing portion.

4. The mask system of claim 3, wherein the second side of the clip portion is adhered to the interfacing portion.

5. The mask system of claim 2, wherein the common frame includes a channel formed by inner and outer ribs.

6. The mask system of claim 5, wherein each clip portion is adapted to be received in the channel with an interference seal to thereby removably attach a corresponding one of the first cushioning element and second cushioning element to the common frame.

7. The mask system of claim 5, wherein the clip portion of the first cushioning element comprises foam.

8. The mask system of claim 7, wherein the clip portion of the first cushioning element includes one or more slots formed in the foam of the clip portion to receive the inner and/or the outer ribs of the common frame.

9. The mask system of claim 2, wherein, in a cross-sectional view, the clip portion of the first cushioning element is narrower than the interfacing portion in a radial direction of the first cushioning element.

10. The mask system of claim 9, wherein an unsupported inner region of the interfacing portion overhangs the clip portion.

11. The mask system of claim 10, wherein the unsupported inner region of the interfacing portion is configured to, in use, bend and conform to the patient's face upon engagement with the patient's face.

12. The mask system of claim 11, wherein the unsupported inner region of the interfacing portion is configured to, in use, engage a nasal bridge region of the patient's face.

13. The mask system of claim 9, wherein the clip portion and the interfacing portion of the first cushioning element are aligned at their outer perimeters.

14. The mask system of claim 2, wherein neither-inner perimeters of the clip portion and the interfacing portion of the first cushioning element are not aligned with one another and outer perimeters of the clip portion and the interface portion of the first cushioning element are not aligned with one another.

15. The mask system of claim 1, wherein the resilient foam of the first cushioning element is an unskinned resilient viscoelastic polyurethane foam.

16. The mask system of claim 1, wherein the interfacing portion has an air permeability in the range of about 0 to about 50 $L/s/m^2$.

17. The mask system of claim 1, wherein the first cushioning element includes a clip portion,
wherein the clip portion has a first side adapted to couple with the common frame and a second side adhered to a contact region of the interfacing portion, and
wherein an overhanging region of the interfacing portion of the first cushioning element extends beyond the clip portion and is configured to flex over the clip portion when the patient's face engages with the interfacing portion in use.

18. The mask system of claim 17, wherein, in a cross-sectional view, a width of the clip portion is narrower than a width of the interfacing portion in a radial direction of the first cushioning element.

19. The mask system of claim 18, wherein an outer perimeter of the clip portion and an outer perimeter of the interfacing portion are aligned.

* * * * *

UNITED STATES PATENT AND TRADEMARK OFFICE
CERTIFICATE OF CORRECTION

| | |
|---|---|
| PATENT NO. | : 12,383,687 B2 |
| APPLICATION NO. | : 17/377558 |
| DATED | : August 12, 2025 |
| INVENTOR(S) | : Lee James Veliss et al. |

It is certified that error appears in the above-identified patent and that said Letters Patent is hereby corrected as shown below:

In the Claims

Claim 14, Column 8, Line 1:
"The mask system of claim 2, wherein neither-inner"
Should read:
"The mask system of claim 2, wherein inner"

Signed and Sealed this
Twenty-seventh Day of January, 2026

John A. Squires
*Director of the United States Patent and Trademark Office*